(12) United States Patent
Jang et al.

(10) Patent No.: US 9,567,577 B2
(45) Date of Patent: Feb. 14, 2017

(54) EXPRESSION VECTOR COMPRISING A POLYNUCLEOTIDE ENCODING A MODIFIED GLUTAMINE SYNTHETASE AND A METHOD FOR PREPARING A TARGET PROTEIN EMPLOYING THE SAME

(71) Applicant: ARES TRADING S.A., Aubonne (CH)

(72) Inventors: Hyun Sook Jang, Daejeon (KR); Dong Heon Lee, Daejeon (KR); Sun Kyu Kim, Daejeon (KR); Yong Ho Ahn, Daejeon (KR); Sang Kyung Park, Daejeon (KR)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 14/384,594

(22) PCT Filed: Mar. 5, 2013

(86) PCT No.: PCT/KR2013/001779
§ 371 (c)(1),
(2) Date: Sep. 11, 2014

(87) PCT Pub. No.: WO2013/137583
PCT Pub. Date: Sep. 19, 2013

(65) Prior Publication Data
US 2015/0044753 A1 Feb. 12, 2015

(30) Foreign Application Priority Data
Mar. 12, 2012 (KR) ........................ 10-2012-0025197

(51) Int. Cl.
*C12N 15/85* (2006.01)
*C12N 9/00* (2006.01)
(Continued)

(52) U.S. Cl.
CPC ................. *C12N 9/93* (2013.01); *A61K 35/12* (2013.01); *C07K 14/71* (2013.01);
(Continued)

(58) Field of Classification Search
None
See application file for complete search history.

(56) References Cited

U.S. PATENT DOCUMENTS

| 5,122,464 A | 6/1992 | Wilson et al. |
| 7,294,481 B1 | 11/2007 | Fung |

(Continued)

FOREIGN PATENT DOCUMENTS

KR 10-2005-0023443 3/2005

OTHER PUBLICATIONS

Pu et al., "Rapid establishment of high-producing cell lines using dicistronic vectors with glutamine synthetase as the selection marker", Molecular Biotechnology, vol. 10, No. 1, pp. 17-25, 1998.*

(Continued)

*Primary Examiner* — Robert Mondesi
*Assistant Examiner* — Richard Ekstrom
(74) *Attorney, Agent, or Firm* — Brian C. Trinque; Lathrop & Gage LLP

(57) ABSTRACT

The present invention relates to a vector comprising a polynucleotide encoding a modified glutamine synthetase (GS), and a method for preparing a target protein employing the same. More particularly, the present invention relates to a modified GS having an increased sensitivity to a glutamine synthetase (GS) inhibitor, a polynucleotide encoding the modified GS, a vector comprising the polynucleotide, a transformant comprising the vector, and a method for preparing a target protein using the transformant.

10 Claims, 6 Drawing Sheets

(51) Int. Cl.
*A61K 35/12* (2015.01)
*C07K 14/71* (2006.01)

(52) U.S. Cl.
CPC .. *C12Y 603/01002* (2013.01); *C07K 2319/30* (2013.01); *C12N 15/85* (2013.01); *C12N 2840/203* (2013.01)

(56) References Cited

U.S. PATENT DOCUMENTS

| | | | |
|---|---|---|---|
| 2005/0048608 A1 | 3/2005 | Chan et al. | |
| 2005/0084928 A1* | 4/2005 | Birch | C07K 14/505 435/69.1 |
| 2015/0337331 A1* | 11/2015 | Takahashi | C12N 15/85 435/34 |

OTHER PUBLICATIONS

NCBI GenBank Accession No. XP_003502909, "Predicted: glutamine synthetase-like [Cricetulus griseus]", 2011, 1 pages.

Pu et al., "Rapid establishment of high-producing cell lines using dicistronic vectors with glutamine synthetase as the selection marker", Molecular Biotechnology, 1998, 10(1), 17-25, English Abstract only.

Omasa, T., "Gene Amplification and its Application in Cell and Tissue Engineering", Journal of Bioscience and Bioengineering, 2002, 94(6), 600-605.

* cited by examiner

| Culture period after transfection | 0 | 5 | 7 | 14 |
|---|---|---|---|---|
| MSX | - | - | 25μM | 25μM |
| Gln | - | + | - | - |

| Culture period after transfection | 3 | 6 | 13 | 20 | 27 |
|---|---|---|---|---|---|
| MSX | - | 25μM | 25μM | 25μM | 200μM |
| Gln | - | - | - | - | - |

EXPRESSION VECTOR COMPRISING A POLYNUCLEOTIDE ENCODING A MODIFIED GLUTAMINE SYNTHETASE AND A METHOD FOR PREPARING A TARGET PROTEIN EMPLOYING THE SAME

This application is a US national phase of International Application No. PCT/KR2013/001779 filed on Mar. 5, 2013, which claims priority to Korean Patent Application No. 10-2012-0025197 filed on Mar. 12, 2012.

TECHNICAL FIELD

The present invention relates to a vector comprising a polynucleotide encoding a modified glutamine synthetase (GS), and a method for preparing a target protein employing the same. More particularly, the present invention relates to a modified GS having an increased sensitivity to a glutamine synthetase (GS) inhibitor, a polynucleotide encoding the modified GS, a vector comprising the polynucleotide, a transformant comprising the vector, and a method for preparing a target protein using the transformant.

BACKGROUND ART

Recombinant proteins can be expressed in different types of host cells including prokaryotic and eukaryotic cells. However, glycoproteins, such as antibodies and Fc fusion proteins, consist of a polypeptide linked to a carbohydrate moiety which influences the safety and efficacy thereof, and thus they are usually expressed in animal cells that are capable of glycosylation during post-translational modification. In the production of recombinant protein drugs, the difference in their sugar chains with those of human (native) glycoproteins is associated with immunogenicity of the protein drugs. Thus, it is important to produce glycoproteins having sugar chains identical or similar to those of human glycoproteins.

Until recently, animal cells such as hybridoma, mouse myeloma, and CHO cells have been commonly used in the expression and production of recombinant protein drugs. The protein expression in these animal cells is appropriate for producing proteins similar to human proteins, but there are disadvantages of a significantly low expression yield and difficulty in scale-up of the production. In particular, therapeutic antibodies need to be produced in kilogram quantities, and thus animal cell culturing is not suitable for a large-scale production of the therapeutic antibodies. Therefore, for a high level expression of a target gene in the host cells, the target gene needs to be integrated into a transcriptionally active region of the genome when the target DNA is randomly introduced to the animal cell. The introduced foreign gene replicates along with the genome of the host cell. However a homologous recombination technique for integration of the gene into transcriptionally active regions is not generalized for common use yet.

Another method for increasing the expression rate of randomly integrated DNA is by amplifying the integrated gene, and this method needs the step of cloning the gene into the vector engineered with gene amplification system. A DHFR system (Takeshi omasa, gene amplification and its application in cell and tissue engineering, J. Bios. and Bioe (2002), Vol. 94, No. 6, 600-605) is a common gene amplification system, and this system increases the protein expression level by co-amplification of a target gene and DHFR using methotrexate (MTX) which is an inhibitor of dihydrofolate reductase (DHFR). DHFR is an enzyme involved in nucleotide biosynthesis, and thus inhibition of DHFR activity can effectively interrupt DNA synthesis which is essential for cell maintenance, thereby leading to cell death. Therefore, only those clones having exogenous DHFR gene inserted in their genome can survive under this condition. Furthermore, when the concentration of MTX being added is increased and a strong promoter is used, DHFR gene can be amplified to hundreds to thousands of copies. That is, the more MTX, a DHFR inhibitor, is added to the cell culture, in order for them to survive they increase the expression of DHFR along with the introduced target gene. Consequently, several copies of DNA will be incorporated, leading to the generation of various molecular variants.

A DHFR system using CHO cell line has been reported and commercialized as an expression system for various protein drugs, verifying its safety and efficacy in use. However, the DHFR system has a disadvantage in that it requires several months to isolate a single cell line that shows the expression level higher than the normal level. In addition, when the cell becomes resistant to MTX, even with an increase in MTX concentration, the target gene cannot be amplified anymore. Furthermore, in the CHO DUKX cells used for DHFR system, revertants may appear easily. As a result, there has been a high demand for the development of a high-level gene expression system for protein production other than the DHFR system.

GS system is a high-level gene expression system that was first developed by Celltech (U.S. Pat. No. 5,122,464), and it overcame the limitations of the DHFR-based gene expression system, that is, low time-efficiency for isolating the single cell line of interest and low productivity of target protein. The GS system utilizes glutamine synthetase (GS) which is an enzyme involved in the sole synthetic pathway for producing glutamine from glutamate and ammonia, based on the fact that animal cells cannot grow properly in the glutamine-deficient condition. The GS system has advantage in that it requires less number of DNA copies per cell compared to the DHFR system and allows for the selection of single cell line having high expression rate at the early stage of screening. Consequently, an increasing number of organizations adopt the GS system as a protein drug expression system. NS0 cell line and CHO cell line are the most commonly used cell lines for GS system. Between two, NS0 cell line which is a mouse myeloma cell line cannot express sufficient amount of GS, and thus in the glutamine-deficient condition, those cells where the target gene is inserted into their genome can be easily selected. Unlike the NS0 cell line, a CHO cell line can express sufficient amount of GS that they can survive even in the glutamine-deficient medium. However, if the CHO cells are treated with a high concentration of GS-specific inhibitor such as methionine sulphoximine (MSX), the cells cannot survive only with the endogenous GS activity, and thus only those cells introduced with the vector comprising the GS gene and the gene for a target protein can survive. Through the above mechanism, the cells inserted with the gene for target protein can be isolated, and the target protein can be produced at high yield. In other words, as more GS-specific inhibitor is added to the cells, in order for them to survive, they will amplify exogenous GS gene as well as the target gene which is introduced together with the GS gene, thereby increasing the amount of target protein in the cell. However, even this GS system has a limitation in production amount when the cells transfected with the vector comprising the genes for target protein and GS are treated with the GS-specific inhibitor for producing the target protein. Also when the cells were cultured for a long time, the production amount of the target protein was reduced. Due to these limitations, there has been a high demand for the development of a modified GS protein that responses more sensitively to the GS inhibitor and thus can amplify the target gene introduced with GS to the greater level.

DISCLOSURE OF INVENTION

Technical Problem

In an effort to develop a modified GS protein that has a significantly higher sensitivity to GS inhibitor compared to the wildtype GS protein, the present inventors have developed a modified GS with a significantly higher sensitivity to GS inhibitor having one amino acid substituted compared to the wildtype GS protein. Then, the present inventors confirmed the production of the target protein in the presence of GS inhibitor after transfecting the animal cells with the vector comprising the gene encoding the modified GS and target protein, and further confirmed that the modified GS demonstrates high sensitivity towards GS inhibitor, showing the remarkably higher level of target protein production compared to the vector system comprising the wildtype GS protein and also no reduction in the production level of target protein even after long period of culturing, thereby completing the present invention.

Solution to Problem

An object of the present invention is to provide a modified glutamine synthetase (GS), wherein glycine (Gly, G) at position 299 of a glutamine synthetase having an amino acid sequence shown in SEQ ID NO. 4 is substituted with arginine (Arg, R).

Another object of the present invention is to provide a polynucleotide encoding the modified glutamine synthetase.

Still another object of the present invention is to provide a vector for the expression of a target protein, comprising the polynucleotide and the gene encoding the target protein.

Still another object of the present invention is to provide a transformant comprising the vector.

Still another object of the present invention is to provide a method for the preparation of a target protein comprising culturing of the transformant and to provide the target protein prepared by said method.

Advantageous Effects of Invention

The expression vector comprising a modified GS gene of the present invention allows for the selection of the host cells introduced with the expression vector comprising the modified GS gene even under the condition where CHO cells are used as a host cell and the cells are treated with a GS inhibitor. Therefore, the present expression vector can be widely used for the efficient production of a target protein.

BEST MODE FOR CARRYING OUT THE INVENTION

Figure 1:
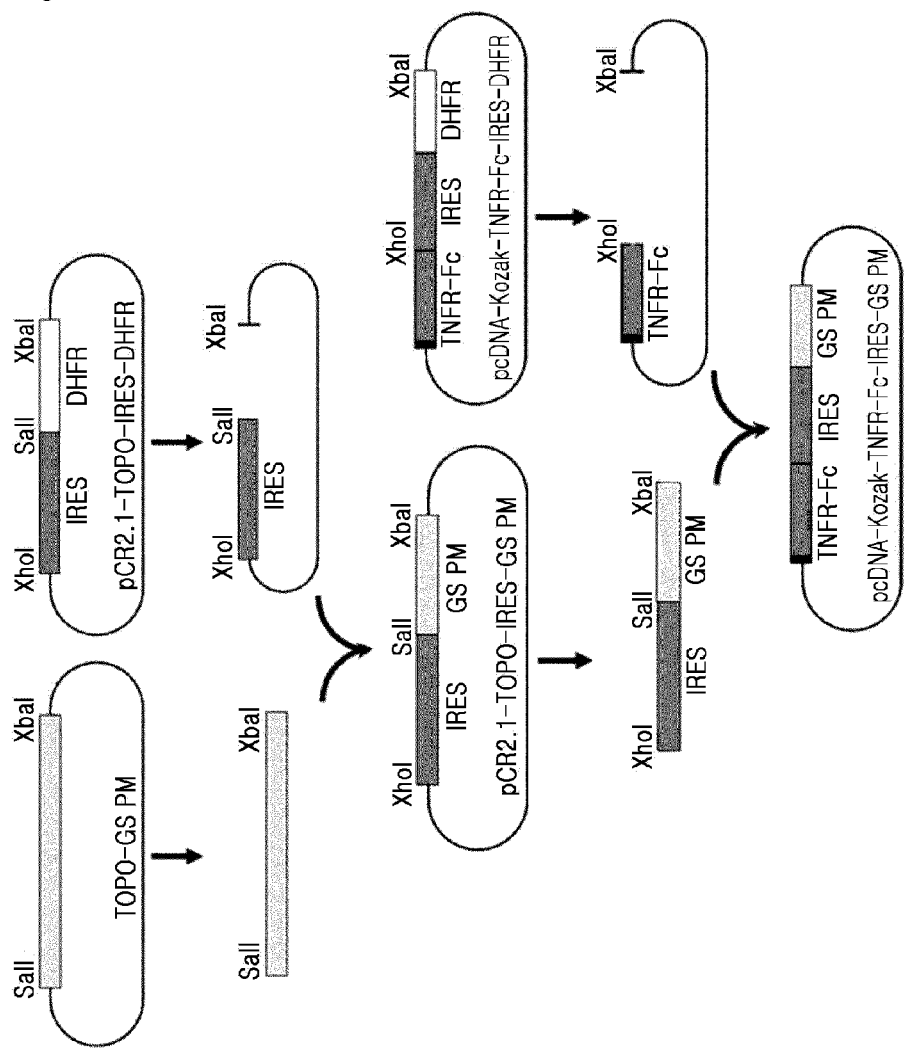
FIG. 1 is a schematic diagram showing the cloning method for preparing pcDNA3.1-Kozak-TNFR-Fc-IRES-GS or pcDNA3.1-kozak-TNFR-Fc-IRES-GS PM of the present invention.

As one aspect, the present invention provides a modified glutamine synthetase (GS), wherein glycine (Gly, G) at position 299 of a glutamine synthetase having an amino acid sequence shown in SEQ ID NO. 4 is substituted with arginine (Arg, R).

As used herein, the term 'glutamine synthetase (GS)' refers to an enzyme that is found in the mammalian organs and microorganisms and that catalyzes the synthesis of glutamine from glutamate and ammonia in the presence of ATP. For activation of this enzyme, divalent metal ions are required, and its enzymatic activity is inhibited by the presence of glycine, alanine, tryptophan, histidine, glucosamine-6-phosphate, cytidine triphosphate, etc. For the purpose of the present invention, the glutamine synthetase refers to an enzyme that can be used to select the cells transfected with the vector comprising the gene encoding a target protein or to enhance the expression of the target protein by treatment with GS inhibitor, but is not limited thereto.

The information on the glutamine synthetase can be obtained from the common database such as NCBI GenBank. For instance, the information on glutamine synthetase derived from hamster can be found from GenBank with the accession number X03495.1, but is not limited thereto. The nucleotide sequence of the representative wild type glutamine synthetase is shown as SEQ ID NO. 3 and its amino acid sequence is shown as SEQ ID NO. 4.

As used herein, the term 'modified glutamine synthetase' refers to an enzyme wherein glycine (Gly, G) at position 299 of a glutamine synthetase modified glutamine synthetase (GS), wherein glycine (Gly, G) at position 299 of a glutamine synthetase having an amino acid sequence shown in SEQ ID NO. 4 is substituted with arginine (Arg, R).

The modified glutamine synthetase may be used as a selection marker by transfection of the cells that can or cannot produce GS endogenously with the target protein expression vector comprising the gene encoding the modified glutamine synthetase, or preferably refers to the protein that can enhance the target protein expression by treatment with GS inhibitor through polycistronic translation with the gene encoding the target protein in the form of 'polynucleotide encoding the promoter-target protein encoding gene-IRES-modified glutamine synthetase' or 'polynucleotide encoding the promoter-modified glutamine synthetase-IRES-target protein encoding gene', but is not limited thereto.

The inventor of the present invention has identified for the first time that if guanosine (G) in the codon of glycine at position 299 of the glutamine synthetase with SEQ ID NO. 4 is substituted with cytidine (C), the sensitivity of glutamine synthetase towards GS inhibitor is remarkably increased, as compared to the wild type GS. As the modified GS of the present invention has a significantly higher sensitivity towards GS inhibitor, it can be effectively used in the target protein expression system.

Furthermore, the modified glutamine synthetase comprises the amino acid sequence wherein glycine (Gly, G) at position 299 of a glutamine synthetase consisting of an amino acid sequence of SEQ ID NO. 4 is substituted with arginine (Arg, R), and as long as the enzyme demonstrates increased sensitivity towards GS inhibitor compared to the wildtype GS, the modified glutamine synthetase of the present invention may comprise the amino acid sequence having a sequence homology of 70% or higher, preferably 80% or higher, more preferably 90% or higher, even more preferably 95% or higher, even much more preferably 98% or higher, and most preferably 99% or higher to the above-described amino acid sequence of modified GS.

As used herein, the term 'GS inhibitor' refers to an external factor that is capable of inhibiting the GS activity. Examples of such inhibitor include glycine, alanine, tryptophan, histidine, glucosamine-6-phosphate, cytidine triphosphate, and methionine sulphoximine (MSX), but is not limited thereto. With respect to the objects of the present invention, the GS inhibitor is preferably MSX, but is not limited thereto.

As used herein, the term 'sensitivity' generally refers to the feature of responding to external stimuli. With respect to enzyme, sensitivity refers to the feature of enhancing or reducing enzymatic activity in response to external factors that regulate enzymatic activity. For the purpose of the present invention, the sensitivity refers to the suppression of the GS activity in response to the GS inhibitor, but is not limited thereto.

In one Example of the present invention, the gene encoding the modified glutamine synthetase was to be obtained through cloning the glutamine synthetase from RNA of hamster cells via PCR. The results confirmed that the modified glutamine synthetase was obtained in which glycine (Gly, G) at position 299 of wildtype glutamine synthetase of SEQ ID NO. 4 is substituted with arginine (Arg, R), and it was named GS PM (Example 3). Subsequently, IRES-GS PM was prepared by linking the polynucleotide encoding the modified glutamine synthetase with IRES, which was further connected to the gene encoding the target protein in order to prepare the vector comprising the expression cassette wherein the target protein encoding gene-IRES-GS PM are operably connected together (Example 4). Furthermore, when the target protein was expressed using the vector comprising the modified glutamine synthetase of the present invention, the production level of the target protein was significantly higher than when the wildtype glutamine synthetase was used (Examples 6 and 7).

As another aspect, the present invention provides a polynucleotide encoding the modified glutamine synthetase.

The modified glutamine synthetase of the present invention is characterized by having a substitution of the amino acid at position 299 of wild type GS from glycine to arginine. Thus, DNA codon encoding the amino acid at position 299 of the modified glutamine synthetase may be selected from the group consisting of CGT, CGC, CGA, CGG, AGA and AGG, but is not limited thereto.

Furthermore, the polynucleotide encoding the modified glutamine synthetase of the present invention may be preferably for enhancing the expression of target protein.

The polynucleotide encoding the modified glutamine synthetase of the present invention may be present in the vector to be translated by polycistronic translation with the gene encoding target protein. After transfection of the host cells with the above vector, when the cells are treated with GS inhibitor, the activity of the modified glutamine synthetase expressed from the introduced vector is inhibited, thereby reducing the synthesis of glutamine. However, in order for the cells to survive, glutamine is essential, and thus under the suppression by GS inhibitor those cells tend to synthesize more of the glutamine synthetase. Here, the target protein-encoding gene introduced along with the polynucleotide encoding the modified GS gets amplified as well, and through this mechanism the expression of the target protein can be increased.

As another aspect, the present invention provides a vector for expression of a target protein, comprising the polynucleotide encoding the modified GS and a gene encoding the target protein.

The polynucleotide encoding the modified GS is the same as described above.

As used herein, the term 'target protein' refers to the protein of interest to be produced in the host cells. For the purpose of the present invention, it refers to the protein whose expression is enhanced by the modified glutamine synthetase, but is not limited thereto. The type of target protein is not specifically limited as long as it can be expressed by the vector of the present invention. In one Example of the present invention, tumor necrosis factor receptor (TNFR)-Fc fusion protein was used as a representative target protein that can be expressed by the modified glutamine synthetase of the present invention.

As used herein, the term 'tumor necrosis factor receptor (TNFR)-Fc fusion protein' refers to the product prepared by connecting the entire or a part of TNFR protein with immunoglobulin Fc region by enzymatic action, or the product prepared by expressing two polypeptides into a single polypeptide by genomic manipulation. In the TNFR-Fc fusion protein, the TNFR protein and the immunoglobulin Fc region may be directly linked with each other, or linked via a peptide linker, but is not limited thereto. The polynucleotide encoding the TNFR-Fc fusion protein may be a polynucleotide of SEQ ID NO. 5, but is not limited thereto.

As used herein, the term 'expression vector' refers to a DNA construct comprising an essential control component which is operably linked to an insert gene so that the insert gene is only expressed when introduced into the host cell. The expression vector may be prepared and purified by a standard recombinant DNA technology. The type of the expression vector is not particularly limited, as long as it expresses and produces a target gene in a variety of host cells of prokaryotic and eukaryotic cells. Preferably, the expression vector is a vector capable of producing a large amount of a foreign protein in a similar form to the native protein while it retains a strong promoter activity and a strong expression ability. The expression vector is preferably a vector comprising at least a promoter, a start codon, a gene encoding a target protein, a stop codon, and a terminator. In addition, it may comprise a DNA encoding a signal peptide, an enhancer sequence, untranslated regions at the 5' and 3' ends of a target gene, a selectable marker region or a replicable unit, etc., if desired. Moreover, the type of the expression vector may be a mono-cistronic vector including a polynucleotide encoding one recombinant protein, a bi-cistronic vector including a polynucleotide encoding two recombinant proteins, a poly-cistronic vector including a polynucleotide encoding three recombinant proteins or more. With respect to the objects of the present invention, the expression vector is preferably a mono-cistronic vector including a SV40 promoter or a bi-cistronic vector including an IRES sequence, more preferably, an expression vector including a promoter, a gene encoding a target protein, IRES, and a modified GS gene in this order or an expression vector including a promoter, a modified GS gene, IRES, and a gene encoding a target protein, but is not limited thereto.

According to one embodiment of the present invention, a polynucleotide encoding GS PM was acquired from CHO DG44, and a pGEMT-GS PM vector was obtained by connecting each of the acquired polynucleotides to a pGEMT vector. Subsequently, the pGEMT-GS PM vector was inserted into a cleaved TOPO-IRES-DHFR vector to obtain a pCR2.1-TOPO-IRES-GS PM vector, and an IRES-GS PM fragment was obtained from the vector. The obtained IRES-GS PM fragment was inserted into a cleaved pcDNA-Kozak-TNFR-Fc-IRES-DHFR vector so as to construct a kozak-TNFR-Fc-IRES-GS PM vector ('IRES-GS PM vector') (FIG. 1).

Figure 3:
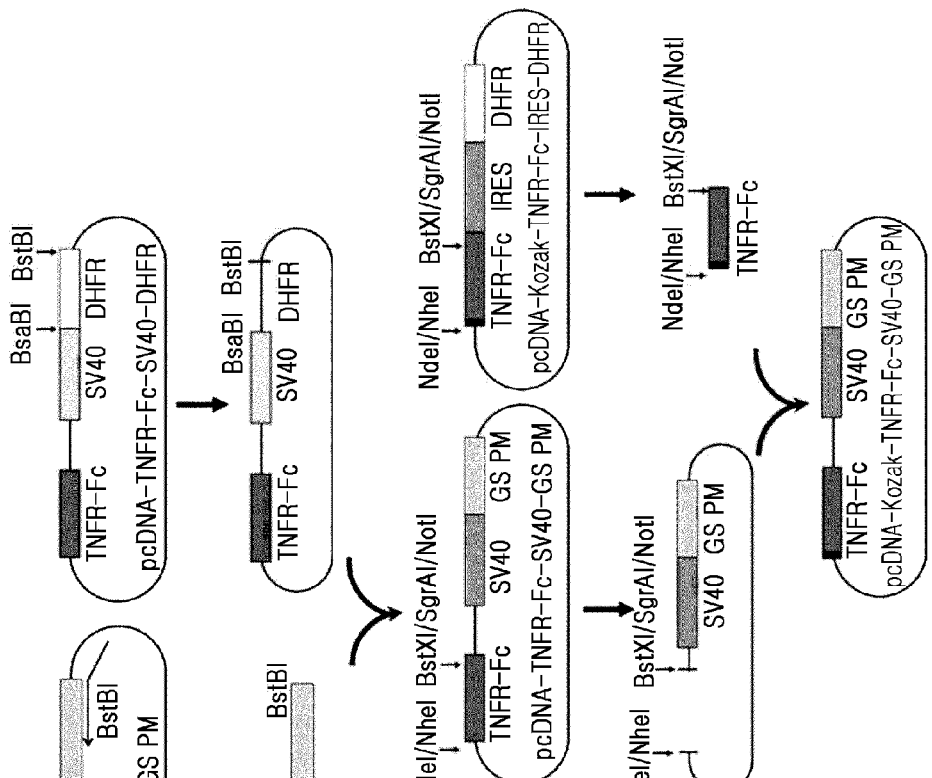
FIG. 3 is a schematic diagram showing the cloning method for preparing the recombinant expression vector, pcDNA3.1-kozak-TNFR-Fc-SV40-GS or pcDNA3.1-kozak-TNFR-Fc-SV40-GS PM, comprising a gene encoding a TNFR-Fc fusion protein which is a representative target protein of the present invention.

According to another embodiment of the present invention, the polynucleotide encoding GS PM was inserted into the cleaved pcDNA3.1-TNFR-Fc-SV40-DHFR vector so as to obtain a pcDNA3.1-TNFR-Fc-SV40-GS PM vector. Thereafter, the pcDNA3.1-TNFR-Fc-SV40-GS PM vector was cleaved, and a TNFR-Fc fragment from the pcDNA3.1-Kozak-TNFR-Fc-IRES-DHFR vector was inserted into the cleaved region so as to construct a pcDNA-Kozak-TNFR-Fc-SV40-GS PM vector ('SV40-GS PM vector') (FIG. 3).

As another aspect, the present invention provides a transformant comprising the vector.

As used herein, the term 'transformant' refers to the cell transformed with the expression vector so as to express the polynucleotide encoding the recombinant protein included in the expression vector. It may be recombinant mammalian cells, rodent cells, preferably animal cells or animal-derived cells, and most preferably NS0 or CHO cells, but is not limited thereto. With respect to the objects of the present invention, the transformant is preferably a transformant prepared by introducing the expression vector into a NS0 or CHO cell line, but is not limited thereto.

As another aspect, the present invention provides a method for preparing a target protein, comprising culturing the transformant.

The transformant and target protein are the same as described above.

To be specific, the above method comprises (a) culturing the transformant; and (b) adding a GS inhibitor to a culture medium. In addition, the method further comprises (c) isolating the target protein from the culture medium.

Preferably, when the GS inhibitor is added to the medium, the expression system using the modified GS protein of the present invention, which has an enhanced sensitivity to GS inhibitor can lead to the increased expression of a target protein as compared to the expression system using the wildtype GS.

As another aspect, the present invention provides a target protein prepared by the above described method.

The method and the target protein are the same as described above.

MODE FOR THE INVENTION

Hereinafter, the present invention will be described in more detail with reference to Examples. However, these Examples are for illustrative purposes only, and the invention is not intended to be limited by these Examples.

Example 1

Synthesis of TNFR-Fc Fusion Protein-Encoding Gene

In order to examine the expression level of a recombinant protein produced using a recombinant protein expression vector system, of the present invention, a TNFR-Fc fusion protein was used as a representative target protein.

The fusion protein-encoding gene (SEQ ID NO. 5) was synthesized by GeneArt Inc., so as to meet the following criteria: (1) it must include a TNFR signal sequence (2) it must express the TNFR amino acids at position 1 to 235 (3) it must be codon-optimized for CHO cells in order to be transfected into CHO cells (4) it must have a NheI restriction site at 5'-end and a NotI restriction site at 3'-end, considering insertion into a pcDNA3.1 vector of Invitrogen.

The nucleotide sequence of the synthesized fusion protein-encoding gene was finally analyzed using the VectorNTI program.

Example 2

Construction of Expression Vector Comprising TNFR-Fc Fusion Protein-Encoding Gene In the present invention, a DHFR system that is a common recombinant protein expression system was utilized as a control for the recombinant protein expression system using the modified GS protein. For this, a hamster dihydrofolate reductase (DHFR) gene was cloned as detailed below:

In order to obtain the hamster DHFR gene, a pSVA3 vector (ATCC 77273) having a mutant type of hamster DHFR gene was purchased, and then a wild type of DHFR gene was obtained by performing point mutation using the DHFR gene as a template. In addition, an IRES sequence was obtained by PCR from a Clontech vector (Cat. #6029-1, PT3267-5) having the corresponding DNA sequence.

The obtained DHFR gene and internal ribosome entry site (IRES) sequence were cloned into a pCR2.1 vector so as to construct a pCR2.1-IRES-DHFR expression vector.

Each of the TNFR-Fc-inserted pcDNA3.1-TNFR-Fc vector obtained in Example 1 and the obtained pCR2.1-IRES-DHFR vector was digested with restriction enzymes, SalI and XbaI, and ligated so as to obtain a TNFR-Fc-inserted pcDNA3.1-TNFR-Fc-IRES-DHFR expression vector.

In order to clone it into a vector having a kanamycin-resistant gene, the kanamycin-resistant gene was obtained from a pAC-GFP vector (#632483) of Clontech, so as to introduce a Kan/Neo gene. The vector is a vector having a Kozak sequence at a transcription initiation sequence of the TNFR-Fc gene and the Kan/Neo gene as an antibiotic selection marker, and it was used as a basic frame for cloning 4 different expression vector systems in order to compare the expression levels of the recombinant protein using CHO cells.

Example 3

Preparation of a Modified GS Gene

In order to acquire a modified GS gene which has an increased sensitivity to GS inhibitor as compared to wild-type GS and thus can be applied to the target protein expression system, the following procedures were performed.

To acquire the modified GS gene, a hamster cell line, CHO DG44 (Invitrogen, 12609-012) was cultured, and then total RNA was isolated using a TRIZOL reagent (Invitrogen). After that, RT-PCR was performed using the obtained total RNA so as to obtain cDNA. PCR (25 cycles of denaturation at 94° C. for 5 minutes; denaturation at 94° C. for 30 seconds, annealing at 50° C. for 30 seconds, elongation at 72° C. for 90 seconds; and elongation at 72° C. for 7 minutes) was performed using the obtained cDNA as a template and a pair of primers (GS SalI-F primer and GS XbaI-R primer) for acquisition of the following GS PM gene, so as to obtain a PCR product.

```
GS SalI-F (Forward primer):
                                      (SEQ ID NO. 6)
5'-gtcgacatggccacctcagcaagttccc-3'

GS XbaI-R (Reverse primer):
                                      (SEQ ID NO. 7)
5'-tctagattagtttttgtattggaaaggg-3'
```

The obtained PCR product was electrophoresed on a 0.8% agarose gel, and then the corresponding band was cut, followed by clean-up using a Quiagen Cleaning kit (#28204). Then, the resultant was inserted into a gene cloning vector, pGEMT vector (Promega, USA). The PCR product-inserted pGEMT vector was introduced into a TOP10 cell so as to obtain a total of 10 colonies. After that, a nucleotide sequence and an amino acid sequence encoded by the nucleotide sequence of each colony were analyzed.

By performing the above procedures numerous times, a modified GS gene showing a difference in one amino acid at position 299 as compared to the amino acid sequence of the wild type hamster GS (NCBI GenBank: X03495.1), was acquired. As a result of sequence analysis, this difference is attributed to the alteration of the 895$^{th}$ nucleotide of the wildtype GS gene (SEQ ID NO. 3) from G (Guanosine) to C (Cytidine). That is, the modified GS has the characteristic of altered amino acids at position 299 from glycine (Gly, G) to arginine (Arg, R). In the present invention, the acquired modified GS was named 'GS PM'.

Further, to acquire a polynucleotide encoding the wild type hamster GS protein, the 895$^{th}$ C in the nucleotide sequence of GS-PM was substituted with G. Specifically, cloning was performed by point mutation for replacement of one amino acid. More specifically, in order to obtain the wild type GS having one amino acid different from those of GS PM of the present invention, PCR (30 cycles of denaturation at 94° C. for 5 minutes; denaturation at 94° C. for 30 seconds, annealing at 54° C. for 30 seconds, elongation at 72° C. for 30 seconds; and elongation at 72° C. for 7 minutes) was performed using the GS PM DNA as a template and a pair of primers (KpnI F-primer and XbaI R-primer) that was synthesized to contain a point mutation region (CGT→GGT). As a result, a GS PCR fragment having an alteration from CGT to GGT was obtained.

```
KpnI F-primer (Forward primer):
                                      (SEQ ID NO. 8)
5'-caccggtaccacattcgagcctacgatcccaagggggggcctggaca atgcccgtggtctg-3'

XbaI R-primer (Reverse primer):
                                      (SEQ ID NO. 9)
5'-tctagattagtttttgtattggaaggg-3'
```

In addition, the nucleotide sequence of the PCR product was analyzed. As a result, a point mutation from CGT to GGT was observed. The corresponding PCR product was digested with KpnI and XbaI, and then ligated with a pGEMT-GS PM vector treated with KpnI and XbaI, so as to obtain a pGEMT-GS vector.

Example 4

Cloning of a Mammalian Cellular Protein-Expressing GS Vector

The GS PM gene included in the pGEMT-GS PM vector obtained in Example 3 was cloned to have SalI and XbaI restriction sites at its N- and C-terminals, respectively. Therefore, in order to obtain IRES-GS PM, a fragment obtained by treating pGEMT-GS PM with SalI and XbaI restriction enzymes was inserted into a TOPO-IRES-DHFR vector that was previously digested with SalI and XbaI restriction enzymes, so as to obtain a pCR2.1-TOPO-IRES-GS PM gene.

Next, in order to connect the TNFR-Fc gene and the IRES-GS PM gene, the TNFR-Fc-IRES-DHFR gene and the IRES-GS PM fragment digested with XhoI and XbaI were ligated so as to construct a kozak-TNFR-Fc-IRES-GS PM vector ("IRES-GS PM vector") (FIG. 1). FIG. 1 is a schematic diagram showing the cloning method of pcDNA3.1-kozak-TNFR-Fc-IRES-GS PM of the present invention.

Figure 2:
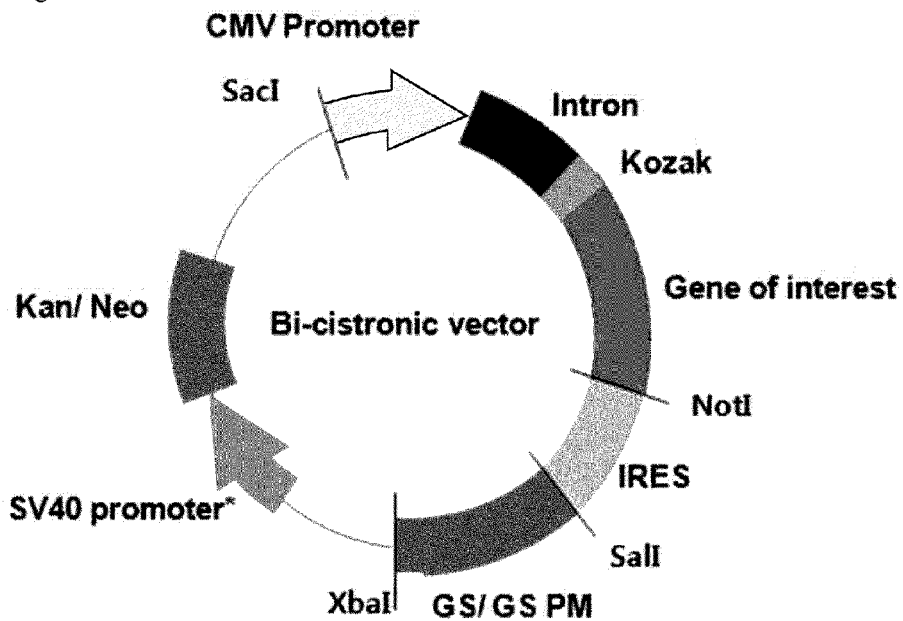
FIG. 2 is a cleavage map of the recombinant expression vector, pcDNA3.1-kozak-TNFR-Fc-IRES-GS or pcDNA3.1-kozak-TNFR-Fc-IRES-GS PM, comprising a gene encoding a TNFR-Fc fusion protein which is a representative target protein of the present invention.

Further, the kozak-TNFR-Fc-IRES-GS PM vector and the TOPO-GS vector were used to construct a Kozak-TNFR-Fc-IRES-GS vector ("IRES-GS vector") (FIG. 2).

FIG. 2 is a cleavage map showing pcDNA3.1-kozak-TNFR-Fc-IRES-GS or pcDNA3.1-kozak-TNFR-Fc-IRES-GS PM, which is a recombinant expression vector including the TNFR-Fc-encoding gene of the present invention.

Meanwhile, the cloned pcDNA3.1-TNFR-Fc-SV40-DHFR vector was used in order to prepare a SV40 promoter-GS system identical to Lonza's GS system among GS systems. Since the pcDNA3.1-TNFR-Fc-SV40-DHFR has no restriction sites suitable for GS gene insertion, new restriction sites were first inserted into both ends of the GS gene.

A pair of primers (GS-BsaBI-F primer and GS-BstBI-R primer) containing BsaBI at the N-terminal of GS gene and BstBI at C-terminal of GS gene were synthesized to perform PCR. Thus, the BsaBI and BstBI sites were inserted into both ends of the GS gene, and DHFR was removed from pcDNA3.1-TNFR-FC-SV40-DHFR by treatment with BsaBI and BstBI. Subsequently, the GS gene digested with BsaBI/BstBI was inserted thereto so as to construct a pcDNA3.1-TNFR-Fc-SV40-GS PM vector.

```
GS-BsaBI-F Primer (forward primer):
                                    (SEQ ID NO. 10)
5'-gatgaggatcatggccacctcagcaag-3'

GS-BstBI-R (reverse primer):
                                    (SEQ ID NO. 11)
5'-ttcgaattagtttttgtattggaaggg-3'
```

However, the pcDNA3.1-TNFR-Fc-SV40-GS PM vector has no Kozak sequence prior to the TNFR-Fc gene, unlike the pcDNA3.1-TNFR-Fc-IRES-GS PM vector. Therefore, a second cloning step of inserting the Kozak sequence into the vector was performed. For the Kozak sequence, a Kozak sequence of the previously prepared pcDNA3.1-Kozak-TNFR-Fc-IRES-DHFR vector was used. Instead of TNFR-Fc of the pcDNA3.1-TNFR-Fc-SV40-GS PM vector, the Kozak-TNFR-Fc was inserted to prepare pcDNA3.1-Kozak-TNFR-FC-SV40-GS PM.

The restriction enzymes to be used for the cloning may include NdeI and NheI at N-terminal of TNFR-Fc and BstXI, SgrAI, and NotI at C-terminal of TNFR-Fc. Available restriction enzymes were selected from them, so as to construct a pcDNA-Kozak-TNFR-Fc-SV40-GS PM vector ("SV40-GS PM vector") (FIG. 3). FIG. 3 is a schematic diagram showing the cloning method of pcDNA3.1-kozak-TNFR-Fc-SV40-GS or pcDNA3.1-kozak-TNFR-Fc-SV40-GS PM, which is a recombinant expression vector including the TNFR-Fc-encoding gene of the present invention.

The constructed SV40-GS PM vector includes an antibiotic resistance gene, ampicillin resistance gene for cell line selection, and thus a third cloning step was performed to replace the gene with a kanamycin resistance gene. The antibiotic resistance gene was replaced by an antibiotic with a low frequency of use on grounds of safety, because ampicillin is one of the antibiotics frequently used by patients.

Figure 4:
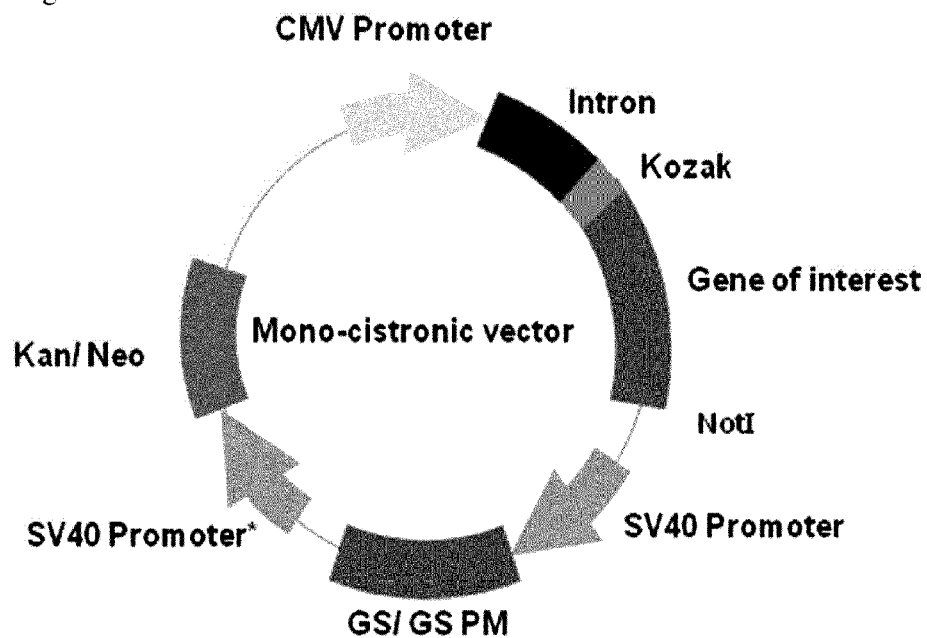
FIG. 4 is a cleavage map of the recombinant expression vector, pcDNA3.1-kozak-TNFR-Fc-SV40-GS or pcDNA3.1-kozak-TNFR-Fc-SV40-GS PM, comprising a gene encoding a TNFR-Fc fusion protein which is a representative target protein of the present invention.

In order to perform the cloning for replacement with the kanamycin resistance gene at a low frequency of use, the kanamycin resistance gene was obtained from the pAC-GFP vector (#632483) of Clontech, and introduced into a SV40-GS PM vector. Furthermore, the SV40-GS PM vector was used to construct a pcDNA-Kozak-TNFR-Fc-SV40-GS vector ('SV40-GS vector') (FIG. 4). FIG. 4 is a cleavage map showing pcDNA3.1-kozak-TNFR-Fc-SV40-GS or pcDNA3.1-kozak-TNFR-Fc-SV40-GS PM, which is a recombinant expression vector including the TNFR-Fc-encoding gene of the present invention.

Finally, 4 different expression vectors of IRES-GS, IRES-GS PM, SV40-GS, and SV40-GS PM were constructed as a protein expression vector system for expressing a target protein in mammalian cells.

Example 5

Preparation of Transformant

In order to compare the productivity of TNFR-Fc fusion protein between the GS and DHFR gene expression systems, each of the expression vectors constructed in Example 4 was introduced into CHO K-1 cells so as to prepare each transformant.

In detail, CHO K-1 cells were cultured in a DMEM/F12 medium supplemented with 10% FBS, and 3 to $4 \times 10^5$ cells/well were inoculated into a 6 well-plate, followed by cultivation overnight. When the cells reached 80 to 90% confluence, each of the expression vectors was introduced thereto.

To achieve this, 4 μg of each of the expression vectors constructed in Example 4 and 250 μl of Opti-MEM were mixed with each other, and separately, 10 μl of Lipofectamine 2000 (Invitrogen) and 250 μl of Opti-MEM were mixed with each other. Then, each mixture was left at room temperature for 5 minutes. Subsequently, the mixtures were mixed with each other, and left at room temperature for 20 minutes.

Thereafter, the culture medium in the 6-well plate was replaced with 2 ml of Opti-MEM I media, and 500 μl of the final mixture was added to each well of the 6-well plate, followed by cultivation at 37° C. for 4 to 6 hours. The medium was replaced with the original culture medium (DMEM/F12 medium supplemented with 10% FBS), followed by further cultivation overnight. Then, the culture medium in the 6-well plate was replaced with a GS selection medium, and subculture was performed according to the growth rate of the cells introduced with each of the expression vectors. At this time, the GS selection medium was glutamine-free DMEM or glutamine-free IMDM containing 10% FBS, 1×GS supplement, and the GS inhibitor, MSX. The 1×GS supplement was prepared by including adenosine (500×, 15 mM), cytidine (1000×, 30 mM), uridine (1000×, 30 mM), guanosine (1000×, 3 mM), thymidine (1000×, 10 mM), asparagine (1000×, 500 mM) and glutamic acid (1000×, 500 mM) or a commercially available 50×GS supplement (SAFC) was used after dilution.

Example 6

Assessment of TNFR-Fc Expression Level

The culture broth of each transformant subcultured in Example 5 was applied to ELISA, in order to measure the expression level of each protein expressed from the transformant.

In detail, a 96-well plate was coated with anti-human IgG Fc antibody (Pierce, 31125), and blocked with 1% BSA. Next, the culture broth of each subcultured transformant was added to each well, and reacted. Subsequently, a biotin-conjugated anti-human TNFR antibody (R&D system) as a detection antibody was added to each well, and reacted. Each well was treated with HRP-conjugated streptavidin, and reacted. Finally, each well was treated with TMB for color development so as to examine the expression level of each protein.

Figure 5:
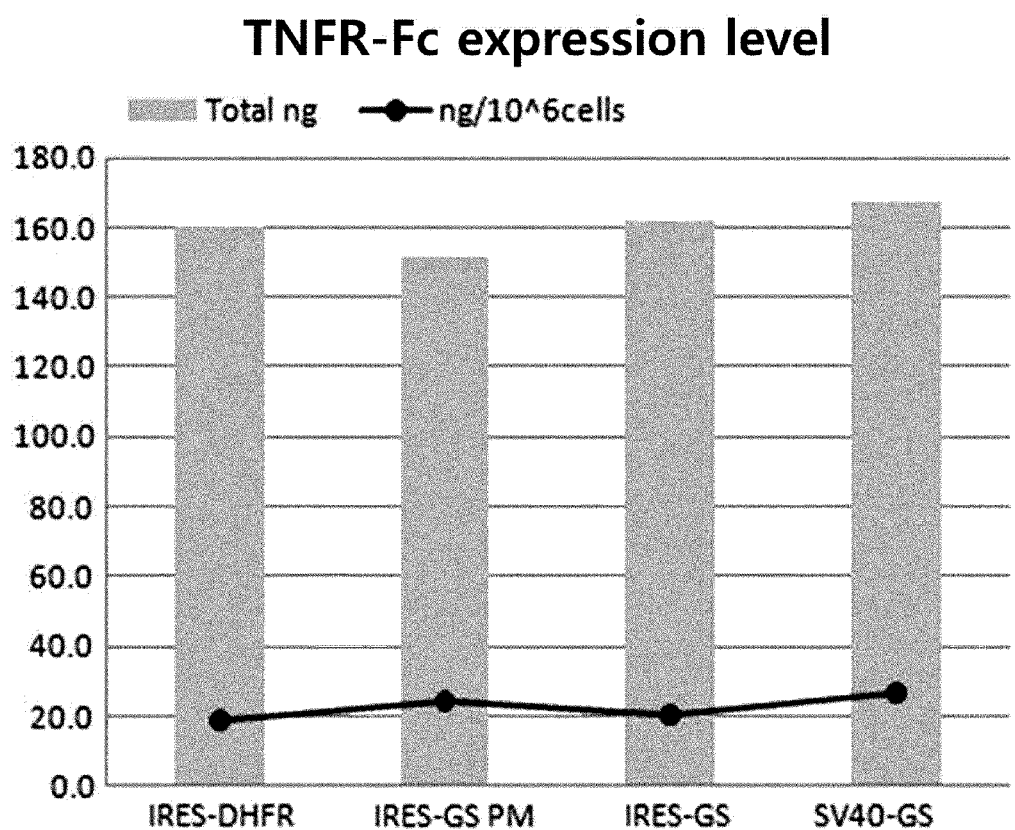
FIG. 5 is a graph showing the expression level of TNFR-Fc in CHO K-1 cells transfected with one of the three types of TNFR-Fc expression vectors (IRES-GS PM, IRES-GS, or SV40-GS)

First, the expression levels in CHO K-1 were compared between three types of TNFR-Fc GS vector (IRES-GS PM, IRES-GS, SV40-GS) and the IRES-DHFR system, and the protein expression levels were also compared between the GS vectors (FIG. 5). FIG. 5 is a graph showing the expression levels of TNFR-Fc in CHO K-1 cells transfected with three types of TNFR-Fc gene expression vector (IRES-GS PM, IRES-GS, SV40-GS).

As a result, as shown in FIG. 5, even at 64 hours after transfection with the expression vectors, CHO K-1 cells showed no changes in the expression level of TNFR-FC protein by three types of GS vectors or in the cell survival rate. Rather, three types of the GS systems were more excellent in terms of expression level than the IRES-DHFR system. Moreover, even at 5 days after transfection of the expression vectors, the cells transfected with the three types of expression vectors maintained their growth and continuously expressed the TNFR-Fc protein.

Figure 6:
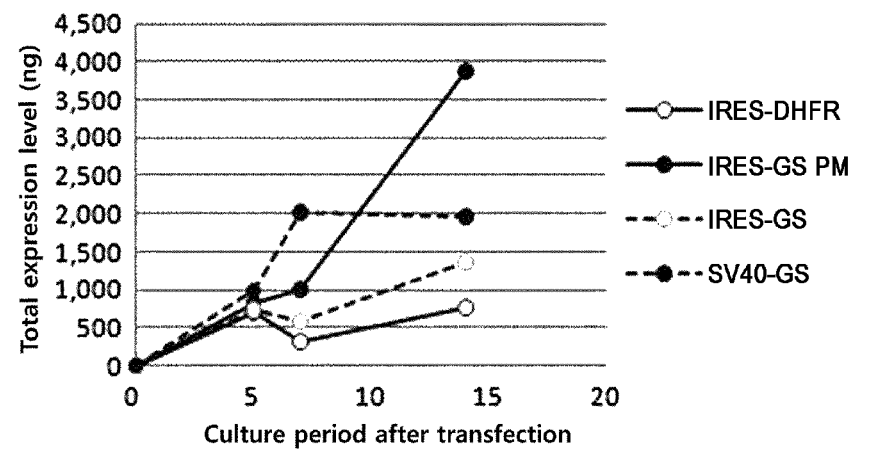
FIG. 6 is a graph showing the changes in expression level of TNFR-Fc protein with MSX treatment over time after transfection of CHO K-1 cells with one of the three types of TNFR-Fc expression vectors (IRES-GS PM, IRES-GS, or SV40-GS)
Figure 6:
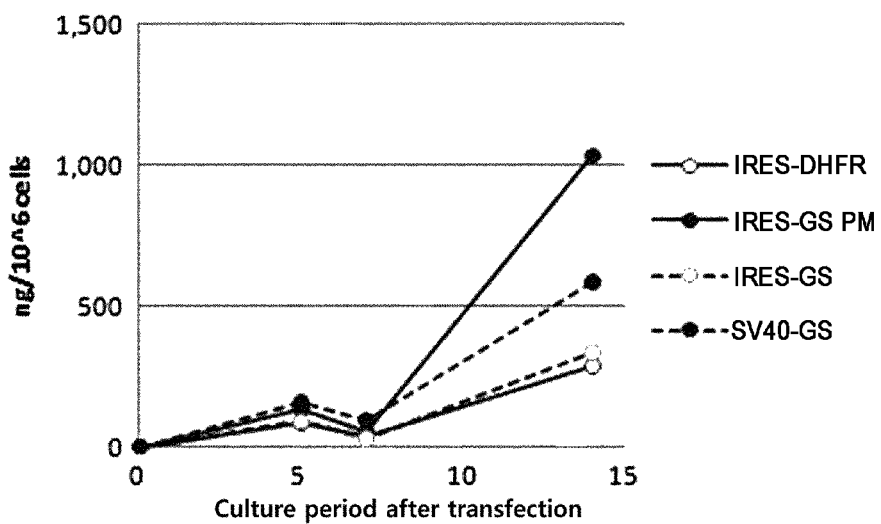

Next, it was also examined whether the same results can be obtained when a glutamine-free selection media containing 25 μM of MSX was used to culture the cells transfected with the three types of the TNFR-Fc gene expression vectors (IRES-GS PM, IRES-GS, SV40-GS) (FIG. 6). FIG. 6 is a graph showing the time-dependent expression level of TNFR-Fc protein according to initial MSX treatment of CHO K-1 cells, which were transfected with the three types of TNFR-Fc gene expression vectors (IRES-GS PM, IRES-GS, SV40-GS).

As shown in FIG. 6, as the cell culture time increased, the cell line transfected with the IRES-GS PM vector of the present invention exhibited higher levels in terms of the total TNFR-Fc protein expression level and the expression level per an equal number of cells, compared to the cell lines transfected with other vectors. Immediately after transfection of the expression vectors, the cells transfected with the SV40-GS vector exhibited the highest level. However, after addition of MSX, the cells transfected with the IRES-GS PM vector of the present invention exhibited the highest level.

Meanwhile, the overall analysis of the results of FIG. 5 showed that there is a great difference in the expression level between the IRES-GS and IRES-GS PM, even though both of them include the identical IRES. At the beginning of the experiment, it was expected that there would be no difference in their activities, because of only one amino acid difference between the two genes. Actually, there was a difference between GS and GS PM, as the cultivation maintained in the selection media.

Figure 7:
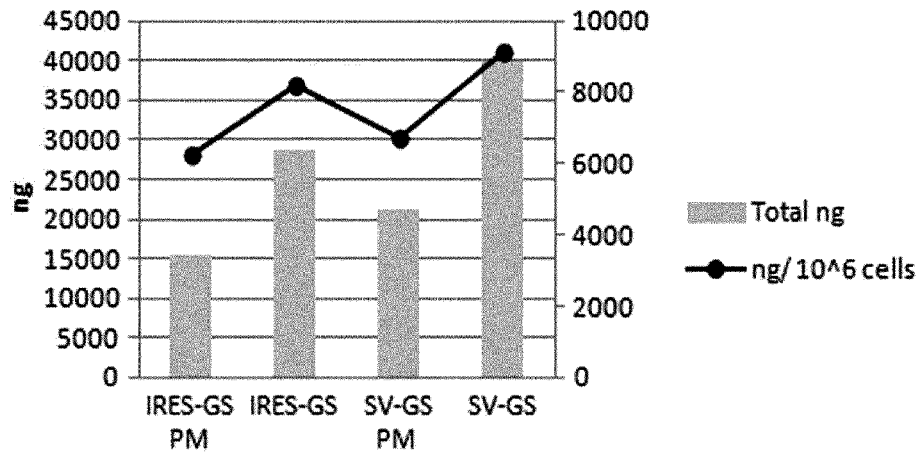
FIG. 7 is a graph demonstrating the changes in TNFR-Fc expression level confirmed by the secondary transient transfection, showing a high expression level in the SV40-GS vector-transfected group during the early phase of culturing, but after longer period of culturing with the MSX treatment the highest expression level was observed in IRES-GS PM vector-transfected group.
Figure 7:
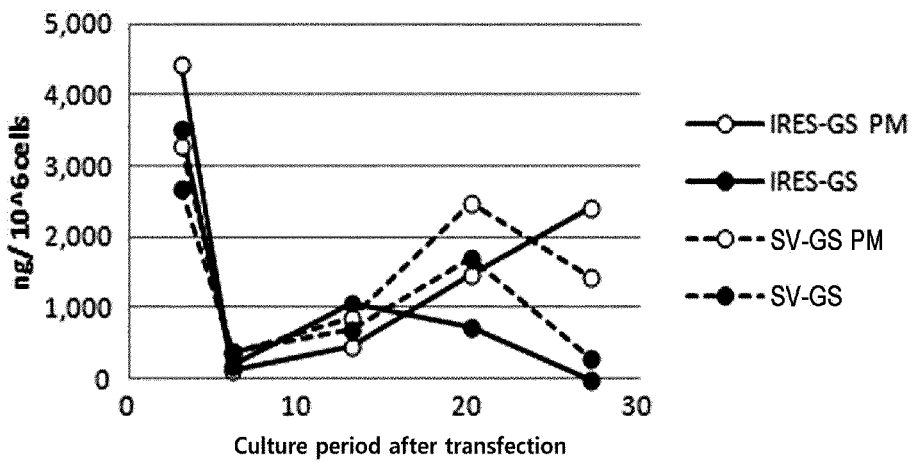

Therefore, in order to clearly examine whether one amino acid difference between GS and GS PM greatly affects the expression level, the SV40-GS PM vector was used to compare the expression levels of TNFR-Fc protein between the cell lines transfected with a total of 4 types of vectors (IRES-GS, IRES-GS PM, SV40-GS, SV40-GS PM) (FIG. 7). FIG. 7 is a graph showing the TNFR-Fc expression level after a secondary transient transfection (upper graph) and the time-dependent TNFR-Fc expression level (lower graph).

As a result, as shown in the upper graph of FIG. 7, the TNFR-Fc expression levels were mostly 6000-9000 ng/$10^6$ cells when the cells were cultured without MSX for 6 days after transfection, and the TNFR-Fc expression levels were relatively increased in the cells transfected with the wild type, IRES-GS and SV40-GS vectors. However, as shown in the lower graph of FIG. 7, when the cells were treated with 25 μM MSX at 3 days after transfection and 200 μM MSX at 20 days after transfection, and then cultured for further 7 days, the TNFR-Fc expression levels were 1000 ng/$10^6$ cells or lower, immediately after the addition of 25 μM MSX, but the expression levels increased according to time. After the addition of 200 μM MSX, only the cells transfected with the IRES-GS PM vector of the present invention showed an increase in the TNFR-Fc expression level.

The above results suggest that the modified GS protein of the present invention shows an enhanced sensitivity to GS inhibitors as compared to that of the wildtype GS protein, and the vector comprising the polynucleotide encoding the modified GS protein and the gene encoding the target protein can be effective to produce the target protein.

Example 7

Comparison of TNFR-Fc Protein Expression Level in Stably Transfected CHO-S Cells The results of Example 6 showed that the higher protein expression level per an equal number of cells was observed in the cell lines transfected with the GS-containing expression vectors (IRES-GS PM and SV40-GS PM expression vectors) among the four types of GS expression vectors. Therefore, the expression levels in the stable CHO-S cell line were compared between the IRES-GS PM and SV40-GS PM expression vectors. In order to produce a large amount of recombinant protein, the CHO-S cell adapted for growth in suspension was used for the stable cell line establishment, instead of CHO K-1.

Figure 8:
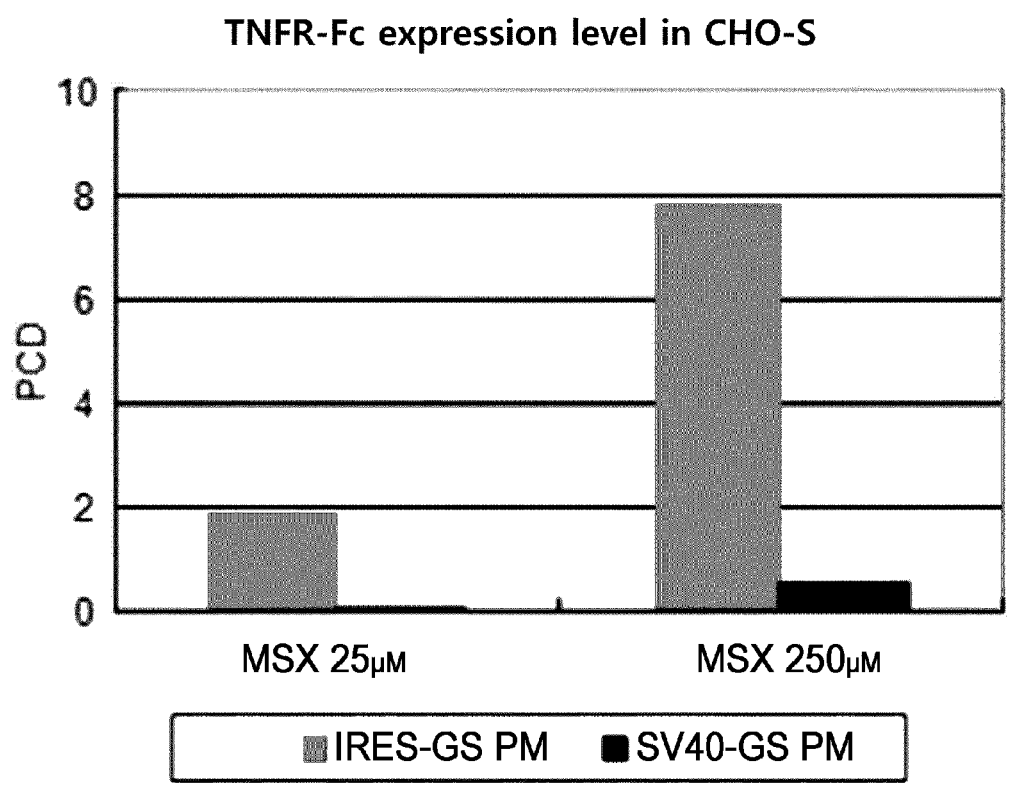
FIG. 8 is a graph showing the TNFR-Fc expression level in two groups of stable CHO-S cell line each transfected with either IRES-GS PM vector or SV40-GS PM vector.

First, TNFR-Fc-expressing cell lines transfected with the IRES-GS PM and SV40-GS PM expression vectors were established. Each of the established TNFR-Fc-expressing cell lines was cultured in a medium containing 25 μM or 250 μM MSX, and the expression levels of TNFR-Fc protein expressed therefrom were compared (FIG. 8). FIG. 8 is a graph showing the comparison in the stable cell line between the IRES-GS PM vector and the SV40-GS PM vector. In this regard, PCD indicates pg/cell/day, and it was calculated from the following Equation.

PCD=expression amount (ng/mL)/((A−B)*Culture day/$LN(A/B)$)/1000

A: Harvest cell conc. (×$10^6$ cells/mL)
B: Seed cell conc. (×$10^6$ cells/mL)

As a result, as shown in FIG. 8, the cells transfected with the IRES-GS PM expression vector showed a higher expression level of TNFR-FC protein than those transfected with the SV40-GS PM expression vector, irrespective of MSX concentration. In addition, the maximum PCD at 250 μM MSX was ~8 PCD, which is higher than that of a single cell line limiting-diluted using the known IRES-DHFR system. When single cell lines are selected from the cell groups of 8 PCD, it was expected to obtain the expression cell lines of higher than 8 PCD.

The above results demonstrate that the expression system using the vector comprising the modified GS gene of the present invention, specifically, the polycistronic vector comprising the modified GS gene of the present invention, can produce the target protein with high efficiency.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non obvious combinations of elements described herein, and claims may be presented in this or a later application to any novel and non-obvious combination of these elements.

The invention claimed is:

1. A vector for expression of a target protein, comprising a polynucleotide encoding a modified glutamine synthetase (GS), wherein glycine (Gly, G) at position 299 of a glutamine synthetase having the amino acid sequence shown in SEQ ID NO. 4 is substituted with arginine (Arg, R) and a gene encoding the target protein.

2. The vector according to claim 1, wherein the polynucleotide is for enhancing the expression of the target protein.

3. The vector according to claim 2, wherein the enhanced expression of the target protein is achieved by increasing the sensitivity of GS to a glutamine synthetase inhibitor.

4. The vector according to claim 1, wherein the target protein is a tumor necrosis factor receptor (TNFR)-Fc fusion protein.

5. The vector according to claim 1, wherein the vector further comprises internal ribosome entry site (IRES).

6. The vector according to claim 5, wherein the vector comprises an expression cassette comprising from 5' to 3', the gene encoding the target protein, internal ribosome entry site (IRES) and the polynucleotide encoding the modified glutamine synthetase.

7. A transformant comprising the vector according to claim 1.

8. The transformant according to claim 7, wherein a host cell for transformation is a NS0 cell or CHO cell.

9. A method for preparation of a target protein, comprising culturing the transformant according to claim 7.

10. The method according to claim 9, which further comprises adding a glutamine synthetase inhibitor to a culture medium.

* * * * *

EX PARTE REEXAMINATION CERTIFICATE (11481st)

United States Patent
Jang et al.

(10) Number: US 9,567,577 C1
(45) Certificate Issued: Mar. 18, 2019

(54) EXPRESSION VECTOR COMPRISING A POLYNUCLEOTIDE ENCODING A MODIFIED GLUTAMINE SYNTHETASE AND A METHOD FOR PREPARING A TARGET PROTEIN EMPLOYING THE SAME

(71) Applicant: ARES TRADING S.A., Aubonne (CH)

(72) Inventors: Hyun Sook Jang, Daejeon (KR); Dong Heon Lee, Daejeon (KR); Sun Kyu Kim, Daejeon (KR); Yong Ho Ahn, Daejeon (KR); Sang Kyung Park, Daejeon (KR)

(73) Assignee: ARES TRADING S.A., De l'Ouriettaz, Aubonne (CH)

Reexamination Request:
No. 90/014,094, Feb. 21, 2018

Reexamination Certificate for:
Patent No.: 9,567,577
Issued: Feb. 14, 2017
Appl. No.: 14/384,594
PCT Filed: Mar. 5, 2013
PCT No.: PCT/KR2013/001779
§ 371 (c)(1),
(2) Date: Sep. 11, 2014
PCT Pub. No.: WO2013/137583
PCT Pub. Date: Sep. 19, 2013

(51) Int. Cl.
*C12N 15/85* (2006.01)
*C07K 14/71* (2006.01)
*A61K 35/12* (2015.01)
*C12N 9/00* (2006.01)

(52) U.S. Cl.
CPC ............... *C12N 9/93* (2013.01); *A61K 35/12* (2013.01); *C07K 14/71* (2013.01); *C12N 15/85* (2013.01); *C12Y 603/01002* (2013.01); *C07K 2319/30* (2013.01); *C12N 2840/203* (2013.01)

(58) Field of Classification Search
None
See application file for complete search history.

(56) References Cited

To view the complete listing of prior art documents cited during the proceeding for Reexamination Control Number 90/014,094, please refer to the USPTO's public Patent Application Information Retrieval (PAIR) system under the Display References tab.

*Primary Examiner* — Bruce R Campell

(57) ABSTRACT

The present invention relates to a vector comprising a polynucleotide encoding a modified glutamine synthetase (GS), and a method for preparing a target protein employing the same. More particularly, the present invention relates to a modified GS having an increased sensitivity to a glutamine synthetase (GS) inhibitor, a polynucleotide encoding the modified GS, a vector comprising the polynucleotide, a transformant comprising the vector, and a method for preparing a target protein using the transformant.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

The patentability of claims 4-6 and 8 is confirmed.

Claims 1-3, 7, 9 and 10 are cancelled.

\* \* \* \* \*

(12) EX PARTE REEXAMINATION CERTIFICATE (11670th)
United States Patent
Jang et al.

(10) Number: US 9,567,577 C2
(45) Certificate Issued: Apr. 6, 2020

(54) EXPRESSION VECTOR COMPRISING A POLYNUCLEOTIDE ENCODING A MODIFIED GLUTAMINE SYNTHETASE AND A METHOD FOR PREPARING A TARGET PROTEIN EMPLOYING THE SAME

(71) Applicant: ARES TRADING S.A., Aubonne (CH)

(72) Inventors: Hyun Sook Jang, Daejeon (KR); Dong Heon Lee, Daejeon (KR); Sun Kyu Kim, Daejeon (KR); Yong Ho Ahn, Daejeon (KR); Sang Kyung Park, Daejeon (KR)

(73) Assignee: ARES TRADING S.A., Aubonne (CH)

Reexamination Request:
No. 90/014,296, May 1, 2019

Reexamination Certificate for:
Patent No.: 9,567,577
Issued: Feb. 14, 2017
Appl. No.: 14/384,594
PCT Filed: Mar. 5, 2013
PCT No.: PCT/KR2013/001779
§ 371 (c)(1),
(2) Date: Sep. 11, 2014
PCT Pub. No.: WO2013/137583
PCT Pub. Date: Sep. 19, 2013

Reexamination Certificate C1 9,567,577 issued Mar. 18, 2019

(30) Foreign Application Priority Data

Mar. 12, 2012 (KR) .......................... 10-2012-0025197

(51) Int. Cl.
| | | |
|---|---|---|
| *C12N 15/85* | (2006.01) | |
| *C07K 14/71* | (2006.01) | |
| *A61K 35/12* | (2015.01) | |
| *C12N 9/00* | (2006.01) | |

(52) U.S. Cl.
CPC ................ *C12N 9/93* (2013.01); *A61K 35/12* (2013.01); *C07K 14/71* (2013.01); *C12N 15/85* (2013.01); *C12Y 603/01002* (2013.01); *C07K 2319/30* (2013.01); *C12N 2840/203* (2013.01)

(58) Field of Classification Search
None
See application file for complete search history.

(56) References Cited

To view the complete listing of prior art documents cited during the proceeding for Reexamination Control Number 90/014,296, please refer to the USPTO's public Patent Application Information Retrieval (PAIR) system under the Display References tab.

*Primary Examiner* — Sharon Turner

(57) ABSTRACT

The present invention relates to a vector comprising a polynucleotide encoding a modified glutamine synthetase (GS), and a method for preparing a target protein employing the same. More particularly, the present invention relates to a modified GS having an increased sensitivity to a glutamine synthetase (GS) inhibitor, a polynucleotide encoding the modified GS, a vector comprising the polynucleotide, a transformant comprising the vector, and a method for preparing a target protein using the transformant.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-3, 7 and 9-10 were previously cancelled.
Claims 4-6 and 8 are cancelled.

\* \* \* \* \*

SEQUENCE LISTING

<160> NUMBER OF SEQ ID NOS: 11

<210> SEQ ID NO 1
<211> LENGTH: 1122
<212> TYPE: DNA

<213> ORGANISM: Artificial Sequence
<220> FEATURE:
<223> OTHER INFORMATION: synthetic-gene encoding a modified GS

<400> SEQUENCE: 1

```
atggccacct cagcaagttc ccacttgaac aaaaacatca agcaaatgta cttgtgcctg      60
ccccagggtg agaaagtcca agccatgtat atctgggttg atggtactgg agaaggactg     120
cgctgcaaaa cccgcaccct ggactgtgag cccaagtgtg tagaagagtt acctgagtgg     180
aattttgatg gctctagtac ctttcagtct gagggctcca acagtgacat gtatctcagc     240
cctgttgcca tgtttcggga ccccttccgc agagatccca acaagctggt gttctgtgaa     300
gttttcaagt acaaccggaa gcctgcagag accaatttaa ggcactcgtg taaacggata     360
atggacatgg tgagcaacca gcaccccctgg tttggaatgg aacaggagta tactctgatg     420
ggaacagatg gcacccttt tggttggcct tccaatggct ttcctgggcc ccaaggtccg      480
tattactgtg gtgtgggcgc agacaaagcc tatggcaggg atatcgtgga ggctcactac     540
cgcgcctgct gtatgctgg ggtcaagatt acaggaacaa atgctgaggt catgcctgcc      600
cagtgggaat ccaaatagg accctgtgaa ggaatccgca tgggagatca tctctgggtg      660
gcccgtttca tcttgcatcg agtatgtgaa gactttgggg taatagcaac ctttgacccc    720
aagcccattc tgggaactg aatggtgca ggctgccata ccaactttag caccaaggcc      780
atgcgggagg agaatggtct gaagcacatc gaggaggcca tcgagaaact aagcaagcgg     840
caccggtacc acattcgagc ctacgatccc aaggggggcc tggacaatgc ccgtcgtctg     900
actgggttcc acgaaacgtc caacatcaac gactttctg ctggtgtcgc caatcgcagt     960
gccagcatcc gcattcccg gactgtcggc caggagaaga aggttactt tgaagaccgc     1020
cgcccctctg ccaattgtga ccctttgca gtgacagaag ccatcgtccg cacatgcctt    1080
ctcaatgaga ctggcgacga gcccttccaa tacaaaaact aa                        1122
```

<210> SEQ ID NO 2
<211> LENGTH: 373
<212> TYPE: PRT
<213> ORGANISM: Artificial Sequence
<220> FEATURE:
<223> OTHER INFORMATION: synthetic-modified GS

<400> SEQUENCE: 2

```
Met Ala Thr Ser Ala Ser Ser His Leu Asn Lys Asn Ile Lys Gln Met
1               5                   10                  15

Tyr Leu Cys Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Glu Leu Pro Glu Trp Asn Phe Asp Gly
    50                  55                  60

Ser Ser Thr Phe Gln Ser Glu Gly Ser Asn Ser Asp Met Tyr Leu Ser
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Asn Gln His
        115                 120                 125

Pro Trp Phe Gly Met Glu Gln Glu Tyr Thr Leu Met Gly Thr Asp Gly
```

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
            165                 170                 175

Glu Ala His Tyr Arg Ala Cys Leu Tyr Ala Gly Val Lys Ile Thr Gly
        180                 185                 190

Thr Asn Ala Glu Val Met Pro Ala Gln Trp Glu Phe Gln Ile Gly Pro
            195                 200                 205

Cys Glu Gly Ile Arg Met Gly Asp His Leu Trp Val Ala Arg Phe Ile
210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys His Ile Glu Glu
            260                 265                 270

Ala Ile Glu Lys Leu Ser Lys Arg His Arg Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 3
<211> LENGTH: 1122
<212> TYPE: DNA
<213> ORGANISM: Cricetulus longicaudatus

<400> SEQUENCE: 3
atggccacct cagcaagttc ccacttgaac aaaaacatca agcaaatgta cttgtgcctg      60
ccccagggtg agaaagtcca agccatgtat atctgggttg atggtactgg agaaggactg     120
cgctgcaaaa cccgcaccct ggactgtgag cccaagtgtg tagaagagtt acctgagtgg     180
aattttgatg gctctagtac ctttcagtct gagggctcca acagtgacat gtatctcagc     240
cctgttgcca tgtttcggga ccccttccgc agagatccca acaagctggt gttctgtgaa     300
gttttcaagt acaaccggaa gcctgcagag accaatttaa ggcactcgtg taaacggata     360
atggacatgg tgagcaacca gcaccgctgg tttggaatgg aacaggagta tactctgatg     420
ggaacagatg gcaccccttt tggttggcct tccaatggct ttcctgggcc ccaaggtccg     480
tattactgtg gtgtgggcgc agacaaagcc tatggcaggg atatcgtgga ggctcactac     540
cgcgcctgct tgtatgctgg ggtcaagatt acaggaacaa atgctgaggt catgcctgcc     600
cagtgggaat tccaaatagg accctgtgaa ggaatccgca tgggagatca tctctggggtg    660
gcccgtttca tcttgcatcg agtatgtgaa gactttgggg taatagcaac ctttgacccc    720

```
aagcccattc ctgggaactg gaatggtgca ggctgccata ccaactttag caccaaggcc    780
atgcgggagg agaatggtct gaagcacatc gaggaggcca tcgagaaact aagcaagcgg    840
caccggtacc acattcgagc ctacgatccc aagggggggcc tggacaatgc ccgtggtctg   900
actgggttcc acgaaacgtc caacatcaac gactttctg ctggtgtcgc caatcgcagt    960
gccagcatcc gcattccccg gactgtcggc caggagaaga aaggttactt tgaagaccgc   1020
cgcccctctg ccaattgtga ccccttttgca gtgacagaag ccatcgtccg cacatgccct   1080
ctcaatgaga ctggcgacga gcccttccaa tacaaaaact aa                      1122
```

<210> SEQ ID NO 4
<211> LENGTH: 373
<212> TYPE: PRT
<213> ORGANISM: Cricetulus longicaudatus

<400> SEQUENCE: 4

```
Met Ala Thr Ser Ala Ser Ser His Leu Asn Lys Asn Ile Lys Gln Met
1               5                   10                  15

Tyr Leu Cys Leu Pro Gln Gly Glu Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Cys Glu Pro Lys Cys Val Glu Leu Pro Glu Trp Asn Phe Asp Gly
    50                  55                  60

Ser Ser Thr Phe Gln Ser Glu Gly Ser Asn Ser Asp Met Tyr Leu Ser
65                  70                  75                  80

Pro Val Ala Met Phe Arg Asp Pro Phe Arg Arg Asp Pro Asn Lys Leu
                85                  90                  95

Val Phe Cys Glu Val Phe Lys Tyr Asn Arg Lys Pro Ala Glu Thr Asn
            100                 105                 110

Leu Arg His Ser Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Thr Gly
            180                 185                 190

Thr Asn Ala Glu Val Met Pro Ala Gln Trp Glu Phe Gln Ile Gly Pro
        195                 200                 205

Cys Glu Gly Ile Arg Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys His Ile Glu Glu
            260                 265                 270

Ala Ile Glu Lys Leu Ser Lys Arg His Arg Tyr His Ile Arg Ala Tyr
        275                 280                 285

Asp Pro Lys Gly Gly Leu Asp Asn Ala Arg Gly Leu Thr Gly Phe His
    290                 295                 300
```

```
Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ala Val Thr
            340                 345                 350

Glu Ala Ile Val Arg Thr Cys Leu Leu Asn Glu Thr Gly Asp Glu Pro
        355                 360                 365

Phe Gln Tyr Lys Asn
    370

<210> SEQ ID NO 5
<211> LENGTH: 1401
<212> TYPE: DNA
<213> ORGANISM: Artificial Sequence
<220> FEATURE:
<223> OTHER INFORMATION: syntehtic - TNFR-Fc

<400> SEQUENCE: 5
```

| | | | | | |
|---|---|---|---|---|---|
| ctgcctgccc | aggtggcctt | cacccottac | gcccctgagc | ctggctccac | ctgccggctg | 60 |
| cgggagtact | acgaccagac | cgcccagatg | tgctgctcca | agtgctcccc | tggccagcac | 120 |
| gccaaggtgt | tctgcaccaa | gacctccgac | accgtgtgcg | acagctgcga | ggactccacc | 180 |
| tacacccagc | tgtggaactg | ggtgcccgag | tgcctgtcct | gcggctcccg | tgctcctcc  | 240 |
| gaccaggtgg | agacccaggc | ctgcacccgg | gagcagaacc | ggatctgcac | ctgcaggcct | 300 |
| ggctggtact | gcgccctgtc | caagcaggag | ggctgccgc  | tgtgcgcccc | tctgcggaag | 360 |
| tgccggcctg | gcttcggcgt | ggccaggcct | ggcaccgaga | ccagcgacgt | ggtgtgcaag | 420 |
| ccttgcgccc | ctggcacctt | ctccaacacc | acctcctcca | ccgacatctg | ccggcctcac | 480 |
| cagatctgca | acgtggtggc | catccctggc | aacgcctcca | tggacgccgt | gtgcacctcc | 540 |
| acctccccca | cccggtctat | ggcccctggc | gctgtgcacc | tgcctcagcc | tgtgtccacc | 600 |
| cggtcccagc | acacccagcc | taccoctgag | ccctccaccg | ccccttctac | cagcttcctg | 660 |
| ctgcctatgg | gcctagccc  | tcctgccgag | ggctccaccg | gcgacgagcc | taagtcctgc | 720 |
| gacaagaccc | acacctgccc | tccctgccct | gcccctgagc | tgctgggcgg | accttccgtg | 780 |
| ttcctgttcc | ctcctaagcc | taaggacacc | ctgatgatct | cccggacccc | tgaggtgacc | 840 |
| tgcgtggtgg | tggacgtgtc | ccacgaggat | cctgaggtga | agttcaattg | gtacgtggac | 900 |
| ggcgtggagg | tgcacaacgc | caagaccaag | cctcgggagg | agcagtacaa | cagcacctac | 960 |
| cgggtggtgt | ccgtgctgac | cgtgctgcac | caggactggc | tgaacggcaa | ggaatacaag | 1020 |
| tgcaaggtgt | ccaacaaggc | cctgcccgct | cctatcgaaa | agaccatctc | caaggccaag | 1080 |
| ggccagcctc | gcgagcctca | ggtgtacacc | ctgcctccct | cccggagga  | gatgaccaag | 1140 |
| aaccaggtgt | ccctgacctg | cctggtgaag | ggcttctacc | cttccgacat | cgccgtggag | 1200 |
| tgggagtcca | acggccagcc | tgagaacaac | tacaagacca | cccctcctgt | gctggactcc | 1260 |
| gacggctcct | tcttcctgta | ctccaagctg | accgtggaca | agtcccggtg | gcagcagggc | 1320 |
| aacgtgttct | cctgctccgt | gatgcacgag | gccctgcaca | accactacac | ccagaagtcc | 1380 |
| ctgtccctga | gccccggcaa | g          |            |            |            | 1401 |

```
<210> SEQ ID NO 6
<211> LENGTH: 28
<212> TYPE: DNA
<213> ORGANISM: Artificial Sequence
<220> FEATURE:
```

```
<223> OTHER INFORMATION: synthetic-GS SalI-F

<400> SEQUENCE: 6
gtcgacatgg ccacctcagc aagttccc                                28

<210> SEQ ID NO 7
<211> LENGTH: 28
<212> TYPE: DNA
<213> ORGANISM: Artificial Sequence
<220> FEATURE:
<223> OTHER INFORMATION: synthetic-GS XbaI-R

<400> SEQUENCE: 7
tctagattag ttttgtatt ggaaaggg                                 28

<210> SEQ ID NO 8
<211> LENGTH: 60
<212> TYPE: DNA
<213> ORGANISM: Artificial Sequence
<220> FEATURE:
<223> OTHER INFORMATION: synthetic-KpnI F-primer

<400> SEQUENCE: 8
caccggtacc acattcgagc ctacgatccc aagggggcc tggacaatgc ccgtggtctg   60

<210> SEQ ID NO 9
<211> LENGTH: 27
<212> TYPE: DNA
<213> ORGANISM: Artificial Sequence
<220> FEATURE:
<223> OTHER INFORMATION: synthetic-XbaI R-primer

<400> SEQUENCE: 9
tctagattag ttttgtatt ggaaggg                                  27

<210> SEQ ID NO 10
<211> LENGTH: 27
<212> TYPE: DNA
<213> ORGANISM: Artificial Sequence
<220> FEATURE:
<223> OTHER INFORMATION: synthetic-GS-BsaBI-F

<400> SEQUENCE: 10
gatgaggatc atggccacct cagcaag                                 27

<210> SEQ ID NO 11
<211> LENGTH: 27
<212> TYPE: DNA
<213> ORGANISM: Artificial Sequence
<220> FEATURE:
<223> OTHER INFORMATION: synthetic-GS-BstBI-R

<400> SEQUENCE: 11
ttcgaattag ttttgtatt ggaaggg                                  27
```